(12) United States Patent
Xu et al.

(10) Patent No.: US 9,688,610 B1
(45) Date of Patent: Jun. 27, 2017

(54) PROCESS PREPARING OF (E)-3-(4-METHOXYPHENYL)-N-METHYL-N-((6,7,8,9-TETRAHYDRO-5H-BENZO-[7]ANNULEN-2-YL)METHYL)PROP-2-EN-1-AMINE

(71) Applicant: Yong Xu, San Diego, CA (US)

(72) Inventors: Yong Xu, San Diego, CA (US); Peter W Yohi, San Diego, CA (US); Michael Xu, San Diego, CA (US); Douglas Cruise, San Diego, CA (US)

(*) Notice: Subject to any disclaimer, the term of this patent is extended or adjusted under 35 U.S.C. 154(b) by 0 days.

(21) Appl. No.: 15/181,339

(22) Filed: Jun. 13, 2016

(51) Int. Cl.
*C07C 209/68* (2006.01)
*C07C 213/08* (2006.01)
*C07C 221/00* (2006.01)

(52) U.S. Cl.
CPC .......... *C07C 213/08* (2013.01); *C07C 209/68* (2013.01); *C07C 221/00* (2013.01); *C07C 2102/12* (2013.01)

(58) Field of Classification Search
None
See application file for complete search history.

(56) References Cited

FOREIGN PATENT DOCUMENTS

CN   WO2015168979   * 11/2015

OTHER PUBLICATIONS

Wang et al. J. Med. Chem. 2016, 59, 4831-4848.*

* cited by examiner

*Primary Examiner* — Clinton Brooks
(74) *Attorney, Agent, or Firm* — Kile Park Reed & Houtteman LLC

(57) ABSTRACT

Provided is a new method for preparing (E)-3-(4-methoxyphenyl)-N-methyl-N-((6,7,8,9-tetrahydro-5H-benzo[7]annulen-2-yl)methyl)prop-2-en-1-amine as a drug intermediate.

16 Claims, No Drawings

PROCESS PREPARING OF (E)-3-(4-METHOXYPHENYL)-N-METHYL-N-((6,7,8,9-TETRAHYDRO-5H-BENZO-[7]ANNULEN-2-YL)METHYL)PROP-2-EN-1-AMINE

FIELD

The present disclosure relates to a chemical medicine field, it relates generally to the new process preparing of (E)-3-(4-methoxyphenyl)-N-methyl-N-((6,7,8,9-tetrahydro-5H-benzo[7]annulen-2-yl)methyl)prop-2-en-1-amine.

BACKGROUND (E)-3-(4-methoxyphenyl)-N-methyl-N-((6 7,8,9-tetrahydro-5H-benzo[7]annulen-2-yl)methyl)prop-2-en-1-amine is a drug intermediate of derivatives of naftifine hydrochloride in WO2015168979A1. It has the structural formula shown as the compound of formula 1:

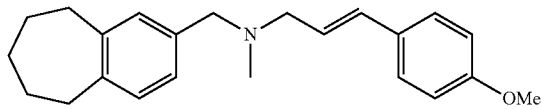

I

The current synthesis method of the compound of formula 1 is still to be improved.

SUMMARY

It is an object of the present disclosure to provide a new method for preparing the compound of formula 1 to improve the process for the synthesis of a compound of formula 1, thereby avoiding at least one of the disadvantages described above.

One aspect of the present disclosure, according to an embodiment of the present disclosure, provides a method for preparing a compound of formula 1. According to some embodiments of the present embodiments, the method for preparing a compound of formula 1 includes the steps of: (1) contacting a compound of formula 2 with acetic anhydride to obtain a compound of formula 3; (2) contacting the compound of formula 3 with a compound of formula 4 to obtain a compound of formula 5; (3) contacting the compound of formula 5 with polyphosphoric acid to obtain a compound of formula 6; (4) contacting the compound of formula 6 with borane-tetrahydrofuran to obtain a compound of formula 7; (5) contacting the compound of formula 7 with sodium hydroxide to obtain a compound of formula 8; and (6) contacting the compound of formula 8 with a compound of formula 9 to obtain the compound of formula 1.

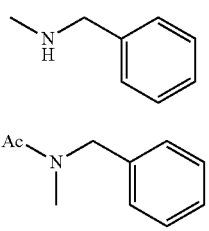

2

3

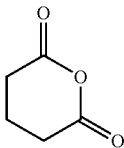

4

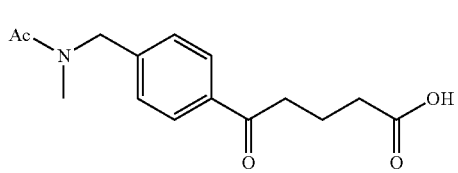

5

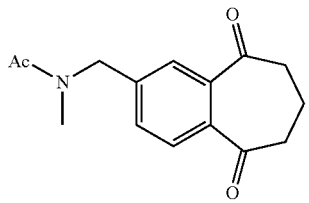

6

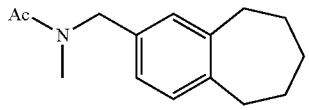

7

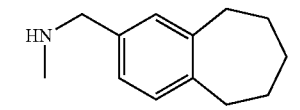

8

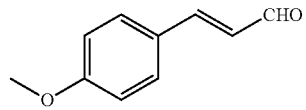

9

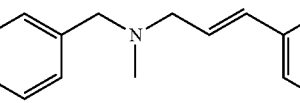

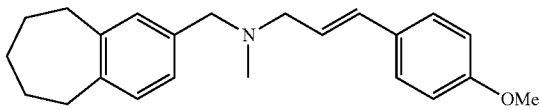

1

It has now been found, surprisingly, in the present invention, the synthesis methods were compared with previously reported WO2015/188309 improve the selectivity of the compound of formula 7 and avoid the α position substituted by products generated, and overcome the disadvantage of low yield of the target product caused by (E)-1-(3-bromoprop-1-en-1-yl)-4-methoxybenzene instability.

According to some embodiments of the present embodiments, in the step (1), to a solution of the compound of formula 2 in dichloromethane (DCM) is added triethylamine, the mixture is cooled to 0° C., acetic anhydride is added dropwise with stirring; after the addition is completed, the reaction is continually stirred for 2 hours to 4 hours, monitored the reaction with TLC and the result showed the reaction was completed, remove the solvent under reduce pressure, and residence is washed with saturated NaHCO₃ aqueous, 10% citric acid aqueous and brine, dried over MgSO₄, filtered and concentrated to give the compound of formula 3.

According to some embodiments of the present embodiments, the amount of triethylamine is 1.2 equivalents per 1 equivalent by mole of the compound of formula 2, so as to improve the synthetic yield of the compound of formula 3.

According to some embodiments of the present embodiments, the amount of acetic anhydride is 1.05 equivalents to 1.3 equivalents per 1 equivalent by mole of the compound of formula 2, so as to improve the synthetic yield of the compound of formula 3.

According to some embodiments of the present embodiments, in the step (2), the compound of formula 3 and the compound of formula 4 are dissolved in 1,2-dichlorobenzene, and the solution is added dropwise into a suspension of $AlCl_3$ in 1,2-dichlorobenzene with stirring, about 20 minutes later, the addition is completed, when there is no more HCl gas released, the reaction mixture is continually stirred for 1 hour, and poured into ice water, the aqueous layer is separated, and ethanol is added, the mixture is stirred and extracted thoroughly, and washed with ethanol repeated; and the mixture is dried under vacuum drying to give the compound of formula 5.

According to some embodiments of the present embodiments, the amount of the compound of formula 4 is 1.01 equivalents to 1.2 equivalents per 1 equivalent by mole of the compound of formula 3, so as to improve the synthetic yield of the compound of formula 5.

According to some embodiments of the present embodiments, the amount of $AlCl_3$ is 2 equivalents per 1 equivalent by mole of the compound of formula 3, so as to improve the synthetic yield of the compound of formula 5.

According to some embodiments of the present embodiments, in the step (3), compound 5 is dissolved in polyphosphoric acid, the mixture is heated to a temperature ranging from about 80° C. to about 95° C., and stirring is kept for 3 hours to 6 hours, the reaction is completed, the mixture temperature is cooled to 45° C., water is poured with stirring, there exist white solid precipitate, and after filtering a filter cake is washed with water three times, after vacuum drying to give compound 6.

According to some embodiments of the present embodiments, the amount of polyphosphoric acid is 10 equivalents to 20 equivalents per 1 equivalent by mole of the compound of formula 5, so as to improve the synthetic yield of the compound of formula 6.

According to some embodiments of the present embodiments, in the step (4), the compound of formula 6 is dissolved in anhydrous THF, the mixture is cooled to 0° C. and protected by anhydrous nitrogen, borane-tetrahydrofuran complex was added dropwise, after the addition is completed, the reaction temperature is raised to room temperature slowly, and stirring is kept for 8 hours to 12 hours, the reaction is quenched by methanol, the solvent is removed under reduced pressure, the residue is dissolved in ethyl acetate, washed with saturated $NaHCO_3$ aqueous, water and brine, dried over anhydrous $Na_2SO_4$, filtered and concentrated to dryness to give the compound of formula 7.

According to some embodiments of the present embodiments, the amount of borane-tetrahydrofuran is 3 equivalents to 5 equivalents per 1 equivalent by mole of the compound of formula 6, so as to improve the synthetic yield of the compound of formula 7.

According to some embodiments of the present embodiments, in the step (5), the compound of formula 7 is dissolved in MeOH/1 N NaOH aq., the mixture is heated to a temperature ranging from about 50° C. to about 70° C. and stirring for 2 hours to 5 hours, the solvent is removed under reduced pressure, and extracted with DCM three times, combined the organic layer, dried over $MgSO_4$, filtered and concentrated to dryness to give the compound of formula 8.

According to some embodiments of the present embodiments, the amount of MeOH is 1 equivalent per 1 equivalent by mole of the compound of formula 7, so as to improve the synthetic yield of the compound of formula 8.

According to some embodiments of the present embodiments, in the step (6), to a solution of the compound of formula 8 in anhydrous MeOH is added the compound of formula 9, the mixture is heated to a temperature ranging from about 50° C. to about 70° C., stirring is kept for 3 hours to 5 hours, the mixture is cooled to 0° C., $NaBH_4$ is added by portions, the reaction mixture is continually stirring at room temperature for 4 hours, the solvent is removed under reduced pressure and the residue is dissolved in ethyl acetate, washed with saturated $NaHCO_3$ aqueous, water and brine, dried over $Na_2SO_4$, filtered and concentrated to give the compound of formula 1.

According to some embodiments of the present embodiments, the amount of the compound of formula 9 is 1 equivalent to 1.5 equivalents per 1 equivalent by mole of the compound of formula 8, so as to improve the synthetic yield of the compound of formula 1.

According to some embodiments of the present embodiments, the amount of $NaBH_4$ is 2 equivalents to 4 equivalents per 1 equivalent by mole of the compound of formula 8, so as to improve the synthetic yield of the compound of formula 1.

DETAILED DESCRIPTION

The term "contacting" herein should be understood broadly, allowing any of at least two reactants react; for example, two reactants to be mixed under appropriate condition. According to the experimental requirements, mixing the reactants with which need to be contacted under stirring. Therefore, the type of agitation is not particularly limited. For example, may be a mechanical agitation, i.e. under the action of mechanical forces stirring.

As used herein, "a compound of formula N" is sometimes also referred to "Compound N". For example, "a compound of formula 2" may also be referred to "compound 2".

In this article, the term "first" or "second" is only used for describing objective other than indicate or imply relative importance or implicit indicate the number of technical features or technical solutions. Thus, defining the "first", the "second" features may explicitly or implicitly includes one or more of the characteristics. In the description of the disclosure, "multiple" means two or more, unless otherwise specifically limited.

According to the present disclosure, it is devised a process of preparing a compound of formula 1:

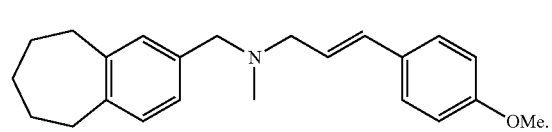

The technical solutions of the present disclosure include: the compound of formula 3 is prepared by a process comprising reacting the compound of formula 2 with acetic anhydride, the compound of formula 5 is prepared by a process comprising reacting the compound of formula 3 with the compound of formula 4, the compound of formula 6 is prepared by a process comprising reacting the compound of formula 5 with polyphosphoric acid, the compound of formula 7 is prepared by a process comprising reacting the compound of formula 6 with borane-tetrahydrofuran, the compound of formula 8 is prepared by a process comprising reacting the compound of formula 7 with sodium hydroxide, the compound of formula 1 is prepared by a process comprising reacting the compound of formula 8 with the compound of formula 9.

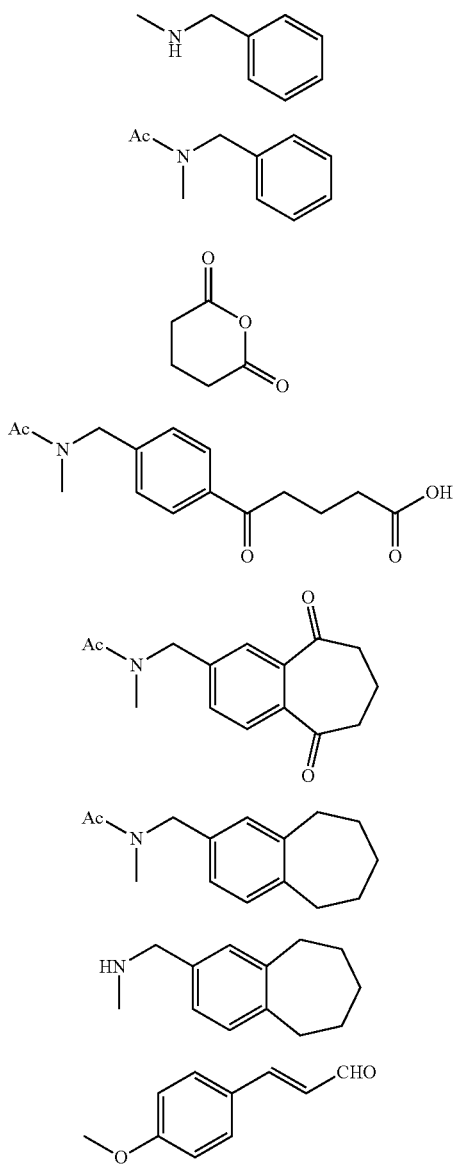

According to some embodiments of the present disclosure, a method for preparing formula 1 of formula 1 includes the following steps:

Step (1): the compound of formula 2 is contacted with acetic anhydride to give the compound of formula 3.

Step (2): the compound of formula 3 is contacted with the compound of formula 4 to give the compound of formula 5.

Step (3): the compound of formula 5 is contacted with polyphosphoric acid to give the compound of formula 6.

Step (4): the compound of formula 6 is contacted with borane-tetrahydrofuran to give the compound of formula 7.

Step (5): the compound of formula 7 is contacted with sodium hydroxide to give the compound of formula 8.

Step (6): the compound of formula 8 is contacted with the compound of formula 9 to give the compound of formula 1.

In some embodiments, in the method disclosed herein, the preparation method of the present invention is as follows.

According to some embodiments of the present disclosure, in the step (1) of the method, to a solution of the compound of formula 2 in DCM was added triethylamine, the mixture was cooling to 0° C., acetic anhydride was added dropwise with stirring. After the addition completed, the reaction was continue stirred for 2 hours to 4 hours, monitored the reaction with TLC and the result showed the reaction was completed, remove the solvent under reduce pressure, and washed with saturated NaHCO$_3$ aqueous, 10% citric acid aqueous and brine, dried over MgSO$_4$, filtered and concentrated to give the compound of formula 3.

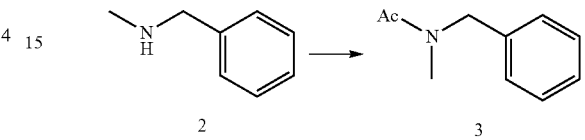

According to some embodiments of the present disclosure, a molar ratio between the compound of formula 2 and acetic anhydride is 1:(1.05-1.3) in the step (1). In other embodiments, the molar ratio between the compound of formula 2 and acetic anhydride is 1:1.1 in the step (1).

According to some embodiments of the present disclosure, a molar ratio between the compound of formula 2 and triethylamine is 1:1.2 in the step (1).

According to some embodiments of the present disclosure, in the step (2) of the method, the compound of formula 3 and the compound of formula 4 was dissolved in 1,2-dichlorobenzene, and the solution was added dropwise into the suspension of AlCl$_3$ in 1,2-dichlorobenzene with stirring, about 20 minutes later, the addition was completed, when there no more HCl gas release, the reaction mixture was continue stirred for 1 hour, and poured into ice water, separated the aqueous layer, and ethanol was added, the mixture was stirred and extracted thoroughly, and washed with ethanol repeated. And then, the mixture was dried under vacuum drying (80° C./120 mbar) to give the compound of formula 5.

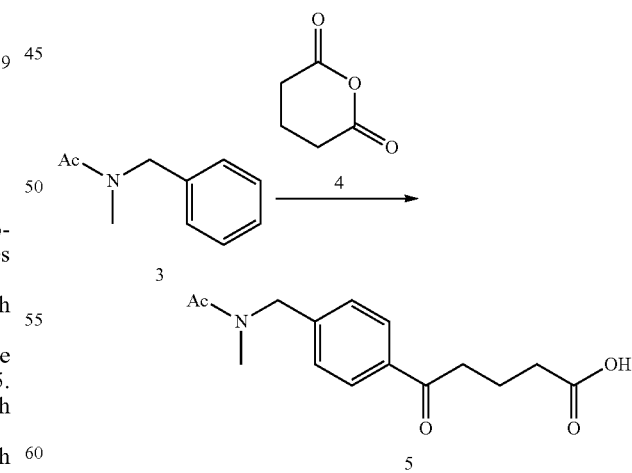

According to some embodiments of the present disclosure, a molar ratio between the compound of formula 3 and the compound of formula 4 is 1:(1.01-1.2) in the step (2). In other embodiments, the molar ratio between the compound of formula 2 and acetic anhydride is 1:1.01 in the step (2).

According to some embodiments of the present disclosure, a molar ratio between the compound of formula 3 and AlCl$_3$ is 1:2 in the step (2).

According to some embodiments of the present disclosure, in the step (3) of the method, compound 5 was dissolved in polyphosphoric acid, the mixture was heated to a temperature ranging from about 80° C. to about 95° C., and keep stirring for 3 hours to 6 hours, the reaction was completed, the mixture temperature was cooling to 45° C., water was poured with stirring, there have white solid precipitate, filtered, and the filter cake was washed with water three times, after vacuum drying to give compound 6.

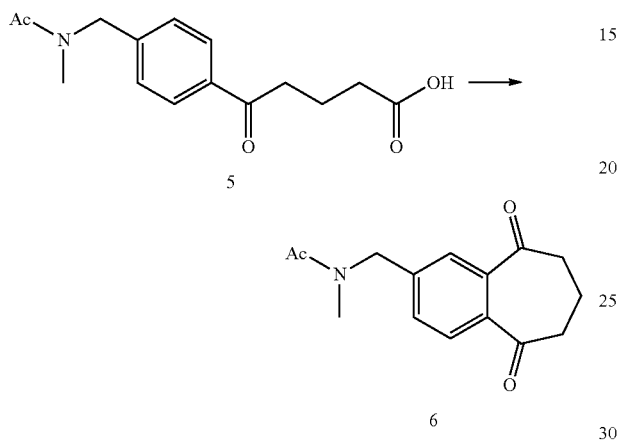

According to some embodiments of the present disclosure, a molar ratio between the compound of formula 5 and polyphosphoric acid is 1:(10-20) in the step (3). In other embodiments, the molar ratio between the compound of formula 2 and acetic anhydride is 1:16.4 in the step (3).

According to some embodiments of the present disclosure, in the step (4) of the method, the compound of formula 6 was dissolved in anhydrous THF, the mixture was cooling to 0° C. and protected by anhydrous nitrogen, borane-tetrahydrofuran complex was added dropwise. After the addition was completed, the reaction temperature was rising to room temperature slowly, and keep stirring for 8 hours to 12 hours, the reaction was quenched by methanol, remove the solvent under reduced pressure, the residue was dissolved in ethyl acetate, washed with saturated NaHCO$_3$ aqueous, water and brine, dried over anhydrous Na$_2$SO$_4$, filtered and concentrated to dryness to give the compound of formula 7.

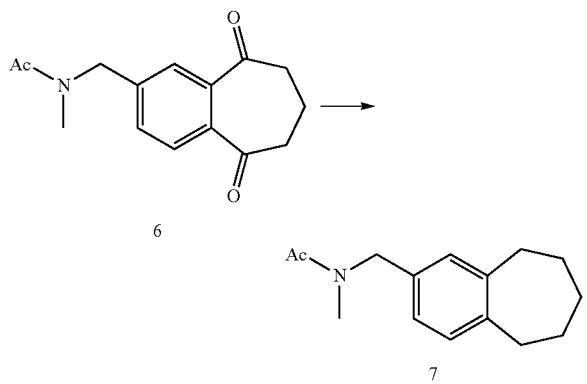

According to some embodiments of the present disclosure, a molar ratio between the compound of formula 6 and borane-tetrahydrofuran is 1:(3-5) in the step (4). In other embodiments, the molar ratio between the compound of formula 2 and acetic anhydride is 1:4 in the step (4).

According to some embodiments of the present disclosure, in the step (5) of the method, the compound of formula 7 was dissolved in MeOH/1 N NaOH aq., the mixture was heated to a temperature ranging from about 50° C. to about 70° C. and stirring for 2 hours to 5 hours, remove the solvent under reduced pressure, and extracted with DCM three times, combined the organic layer, dried over MgSO$_4$, filtered and concentrated to dryness to give the compound of formula 8.

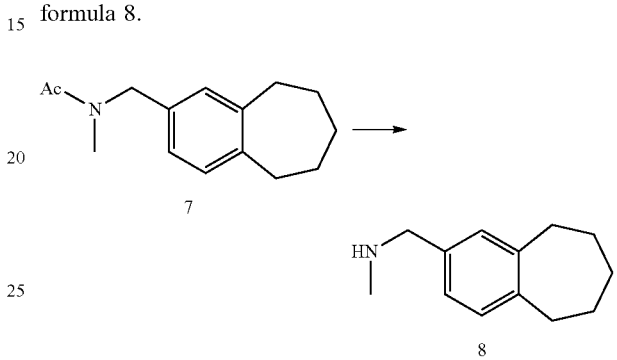

According to some embodiments of the present disclosure, a molar ratio between the compound of formula 7 and NaOH is 1:1 in the step (5).

According to some embodiments of the present disclosure, in the step (5) of the method, to a solution of the compound of formula 8 in anhydrous MeOH was added the compound of formula 9, the mixture was heated to a temperature ranging from about 50° C. to about 70° C., keep stirring for 3 hours to 5 hours, the mixture was cooling to 0° C., NaBH$_4$ was added by portions, the reaction mixture was continue stirring at room temperature for 4 hours. The solvent was removed under reduced pressure and the residue was dissolved in ethyl acetate, washed with saturated NaHCO$_3$ aqueous, water and brine, dried over Na$_2$SO$_4$, filtered and concentrated to give the compound of formula 1.

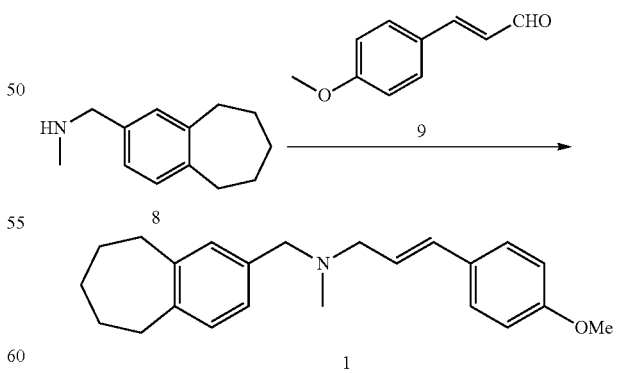

According to some embodiments of the present disclosure, a molar ratio between the compound of formula 8 and the compound of formula 9 is 1:(1-1.5) in the step (6). In other embodiments, the molar ratio between the compound of formula 2 and acetic anhydride is 1:1 in the step (6).

9

According to some embodiments of the present disclosure, a molar ratio between the compound of formula 8 and NaBH₄ is 1:(2-4) in the step (6). In other embodiments, the molar ratio between the compound of formula 2 and acetic anhydride is 1:3 in the step (6).

In the present invention, the term "comprise" is an open expression, it means comprising the contents disclosed herein, but don't exclude other contents.

Compared with the prior art, the advantages of the present invention is as follows:

In the present invention, the synthesis methods were compared with previously reported WO2015/188309 improve the selectivity of the compound of formula 7 and avoid the α position substituted by products generated, and overcome the disadvantage of low yield of the target product caused by (E)-1-(3-bromoprop-1-en-1-yl)-4-methoxybenzene instability. And the whole reaction route is simple, economic and easy to control, has high yield, and does not use harsh conditions such as high temperature and high pressure.

EXAMPLES

The new preparation methods of formula 1 are disclosed in the examples of the present disclosure. Those skilled in the art can learn from this article to properly improve the process parameters to implement the preparation method. It's noted that all the similar replacements and changes are obvious for the skilled person and within the scope of the present disclosure. The methods disclosed herein are described in the preferred examples. Related persons can clearly realize and apply the techniques disclosed herein by making some changes, appropriate alterations or combinations to the methods without departing from spirit, principles and scope of the present disclosure.

In order to further understand the invention, it is detailed below through examples.

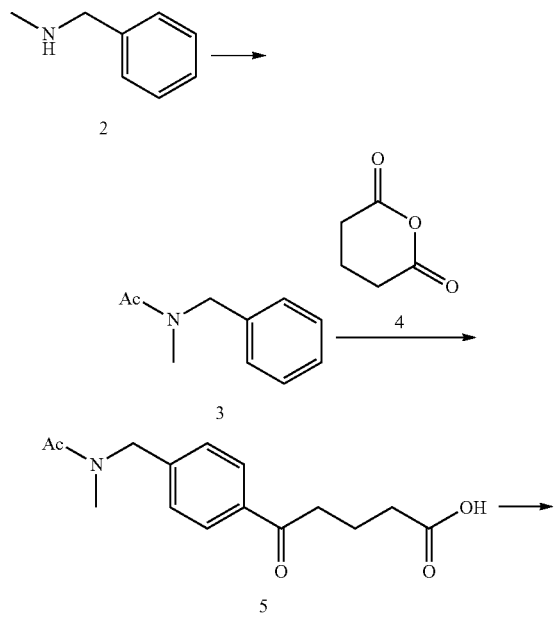

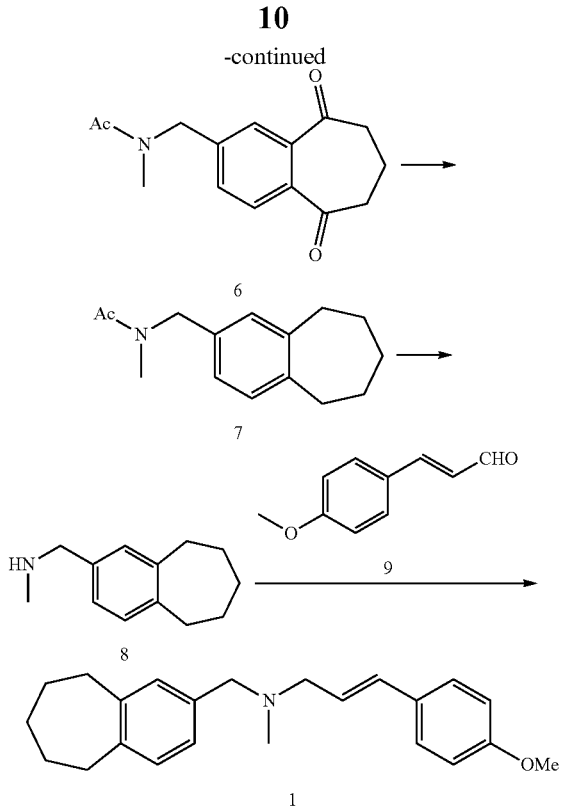

Example 1: Preparation of Compound 3

To a solution of compound 2 (5 g, 41.2 mmol) in DCM (75 mL) was added triethylamine (5.01 g, 49.5 mmol), the mixture was cooling to 0° C., acetic anhydride (4.63 g, 45.38 mmol) was added dropwise with stirring. After the addition completed, the reaction was continue stirred for 3 hours, monitored the reaction with TLC and the result showed the reaction was completed, remove the solvent under reduce pressure, and washed with saturated NaHCO₃ aqueous, 10% citric acid aqueous and brine, dried over MgSO₄, filtered and concentrated to give compound 3 (6.5 g, yield 96.5%).

¹H-NMR (400 MHz, CDCl₃): δ 7.39-7.29 (m, 5H), 4.92 (s, 2H), 3.25 (s, 3H), 2.31 (s, 3H).

Example 2: Preparation of Compound 3

To a solution of compound 2 (5 g, 41.2 mmol) in DCM (75 mL) was added triethylamine (5.01 g, 49.5 mmol), the mixture was cooling to 0° C., acetic anhydride (4.42 g, 43.32 mmol) was added dropwise with stirring. After the addition completed, the reaction was continue stirred for 4 hours, monitored the reaction with TLC and the result showed the reaction was completed, remove the solvent under reduce pressure, and washed with saturated NaHCO₃ aqueous, 10% citric acid aqueous and brine, dried over MgSO₄, filtered and concentrated to give compound 3 (6.2 g, yield 92.0%).

Example 3: Preparation of Compound 3

To a solution of compound 2 (5 g, 41.2 mmol) in DCM (75 mL) was added triethylamine (5.01 g, 49.5 mmol), the mixture was cooling to 0° C., acetic anhydride (5.47 g, 53.63 mmol) was added dropwise with stirring. After the addition completed, the reaction was continue stirred for 2 hours, monitored the reaction with TLC and the result showed the reaction was completed, remove the solvent under reduce pressure, and washed with saturated NaHCO₃ aqueous, 10% citric acid aqueous and brine, dried over MgSO₄, filtered and concentrated to give compound 3 (6.3 g, yield 93.5%).

Example 4: Preparation of Compound 5

Compound 3 (6.5 g, 39.8 mmol) and compound 4 (4.59 g, 40.2 mmol) was dissolved in 1,2-dichlorobenzene (20 ml), and the solution was added dropwise into the suspension of AlCl₃ (10.62 g, 79.6 mmol) in 1,2-dichlorobenzene (25 ml) with stirring, about 20 minutes later, the addition was completed, when there no more HCl gas release, the reaction mixture was continue stirred for 1 h, and poured into 50 ml ice water, separated the aqueous layer, and 100 ml ethanol was added, the mixture was stirred and extracted thoroughly, and washed with ethanol repeated. And then, the mixture was dried under vacuum drying (80° C./120 mbar) to give compound 5 (10.5 g, yield 95%).
$^1$H-NMR (400 MHz, CDCl₃) δ 12.2 (s, 1H), 7.26-7.24 (m, 2H), 6.84-6.82 (m, 2H), 4.92 (s, 2H), 3.25 (s, 3H), 2.96-2.85 (m, 2H), 2.32-2.30 (m, 4H), 1.94-1.88 (m, 2H).

Example 5: Preparation of Compound 5

Compound 3 (6.5 g, 39.8 mmol) and compound 4 (4.77 g, 41.8 mmol) was dissolved in 1,2-dichlorobenzene (20 ml), and the solution was added dropwise into the suspension of AlCl₃ (10.62 g, 79.6 mmol) in 1,2-dichlorobenzene (25 ml) with stirring, about 20 minutes later, the addition was completed, when there no more HCl gas release, the reaction mixture was continue stirred for 1 h, and poured into 50 ml ice water, separated the aqueous layer, and 100 ml ethanol was added, the mixture was stirred and extracted thoroughly, and washed with ethanol repeated. And then, the mixture was dried under vacuum drying (80° C./120 mbar) to give compound 5 (10.5 g, yield 95%).

Example 6: Preparation of Compound 5

Compound 3 (6.5 g, 39.8 mmol) and compound 4 (5.45 g, 47.8 mmol) was dissolved in 1,2-dichlorobenzene (20 ml), and the solution was added dropwise into the suspension of AlCl₃ (10.62 g, 79.6 mmol) in 1,2-dichlorobenzene (25 ml) with stirring, about 20 minutes later, the addition was completed, when there no more HCl gas release, the reaction mixture was continue stirred for 1 h, and poured into 50 ml ice water, separated the aqueous layer, and 100 ml ethanol was added, the mixture was stirred and extracted thoroughly, and washed with ethanol repeated. And then, the mixture was dried under vacuum drying (80° C./120 mbar) to give compound 5 (10.5 g, yield 95%).

Example 7: Preparation of Compound 6

Compound 5 (10.5 g, 37.9 mmol) was dissolved in polyphosphoric acid (210 g, 621.4 mmol), the mixture was heated to 90° C., and keep stirring for 5 hours, the reaction was completed, the mixture temperature was cooling to 45° C., water (250 ml) was poured with stirring, there have white solid precipitate, filtered, and the filter cake was washed with water three times, after vacuum drying to give compound 6 (8.5 g, yield 86.6%).
$^1$H-NMR (400 MHz, CDCl₃) δ 8.06-7.75 (m, 3H), 7.42-7.36 (m, 1H), 4.92 (s, 2H), 3.25 (s, 3H), 2.73-2.64 (m, 4H), 2.31 (s, 3H), 1.67-1.59 (m, 2H).

Example 8: Preparation of Compound 6

Compound 5 (10.5 g, 37.9 mmol) was dissolved in polyphosphoric acid (210 g, 379 mmol), the mixture was heated to 80° C., and keep stirring for 6 hours, the reaction was completed, the mixture temperature was cooling to 45° C., water (250 ml) was poured with stirring, there have white solid precipitate, filtered, and the filter cake was washed with water three times, after vacuum drying to give compound 6 (8.2 g, yield 83.5%).

Example 9: Preparation of Compound 6

Compound 5 (10.5 g, 37.9 mmol) was dissolved in polyphosphoric acid (420 g, 758 mmol), the mixture was heated to 95° C., and keep stirring for 3 hours, the reaction was completed, the mixture temperature was cooling to 45° C., water (250 ml) was poured with stirring, there have white solid precipitate, filtered, and the filter cake was washed with water three times, after vacuum drying to give compound 6 (8.0 g, yield 81.5%).

Example 10: Preparation of Compound 7

Compound 6 (8.5 g, 32.7 mmol) was dissolved in anhydrous THF (150 mL), the mixture was cooling to 0° C. and protected by anhydrous nitrogen, borane-tetrahydrofuran complex (65.5 mL, 2M, 131 mmol) was added dropwise. After the addition was completed, the reaction temperature was rising to room temperature slowly, and keep stirring for 10 hours, the reaction was quenched by methanol, remove the solvent under reduced pressure, the residue was dissolved in ethyl acetate (100 mL), washed with saturated NaHCO₃ aqueous, water and brine, dried over anhydrous Na₂SO₄, filtered and concentrated to dryness to give compound 7 (7.1 g, yield 93.6%).
$^1$H-NMR (400 MHz, CDCl₃) δ 7.19-6.84 (m, 3H), 4.92 (s, 2H), 3.27 (s, 3H), 2.93-2.64 (m, 4H), 2.31 (s, 3H), 1.83 (t, J=8.2 Hz, 2H), 1.74-1.47 (m, 4H).

Example 11: Preparation of Compound 7

Compound 6 (8.5 g, 32.7 mmol) was dissolved in anhydrous THF (150 mL), the mixture was cooling to 0° C. and protected by anhydrous nitrogen, borane-tetrahydrofuran complex (49.1 mL, 2M, 98.2 mmol) was added dropwise. After the addition was completed, the reaction temperature was rising to room temperature slowly, and keep stirring for 12 hours, the reaction was quenched by methanol, remove the solvent under reduced pressure, the residue was dissolved in ethyl acetate (100 mL), washed with saturated NaHCO₃ aqueous, water and brine, dried over anhydrous Na₂SO₄, filtered and concentrated to dryness to give compound 7 (6.9 g, yield 91.0%).

Example 12: Preparation of Compound 7

Compound 6 (8.5 g, 32.7 mmol) was dissolved in anhydrous THF (150 mL), the mixture was cooling to 0° C. and protected by anhydrous nitrogen, borane-tetrahydrofuran complex (81.8 mL, 2M, 163.6 mmol) was added dropwise. After the addition was completed, the reaction temperature was rising to room temperature slowly, and keep stirring for 8 hours, the reaction was quenched by methanol, remove the solvent under reduced pressure, the residue was dissolved in ethyl acetate (100 mL), washed with saturated NaHCO₃ aqueous, water and brine, dried over anhydrous Na₂SO₄, filtered and concentrated to dryness to give compound 7 (6.8 g, yield 89.6%).

Example 13: Preparation of Compound 8

Compound 7 (7 g, 30.3 mmol) was dissolved in MeOH/1 N NaOH aq. (30 mL/30 mL), the mixture was heated to 60° C. and stirring for 3 hours, remove the solvent under reduced pressure, and extracted with DCM three times, combined the organic layer, dried over MgSO₄, filtered and concentrated to dryness to give compound 8 (5 g, yield 87.3%).
$^1$H-NMR (400 MHz, CDCl$_3$) δ 7.19-6.84 (m, 3H), 3.87-3.47 (m, 2H), 2.93-2.64 (m, 4H), 2.47 (d, J=6.6 Hz, 3H), 1.83 (t, J=8.2 Hz, 2H), 1.74-1.47 (m, 4H)

Example 14: Preparation of Compound 8

Compound 7 (7 g, 30.3 mmol) was dissolved in MeOH/1 N NaOH aq. (30 mL/30 mL), the mixture was heated to 50° C. and stirring for 5 hours, remove the solvent under reduced pressure, and extracted with DCM three times, combined the organic layer, dried over MgSO₄, filtered and concentrated to dryness to give compound 8 (4.8 g, yield 83.8%).

Example 15: Preparation of Compound 8

Compound 7 (7 g, 30.3 mmol) was dissolved in MeOH/1 N NaOH aq. (30 mL/30 mL), the mixture was heated to 70° C. and stirring for 2 hours, remove the solvent under reduced pressure, and extracted with DCM three times, combined the organic layer, dried over MgSO₄, filtered and concentrated to dryness to give compound 8 (4.9 g, yield 85.6%).

Example 16: Preparation of Compound 1

To a solution of compound 8 (5.0 g, 26.4 mmol) in anhydrous MeOH (75 ml) was added compound 9 (4.28 g, 26.4 mmol), the mixture was heated to 60° C., keep stirring for 4 hours, the mixture was cooling to 0° C., NaBH4 (3.0 g, 79.2 mmol) was added by portions, the reaction mixture was continue stirring at room temperature for 4 hrs. The solvent was removed under reduced pressure and the residue was dissolved in ethyl acetate (75 ml), washed with saturated NaHCO₃ aqueous, water and brine, dried over Na₂SO₄, filtered and concentrated to give compound 1 (7.8 g, yield 88%).
LCMS: t=2.36 min; MS: 336.23, $^1$H-NMR (400 MHz, MeOD) δ 7.41 (d, J=7.3 Hz, 2H), 7.31-7.13 (m, 5H), 6.88 (d, J=16.2 Hz, 1H), 6.32-6.21 (m, 1H), 4.40 (s, 1H), 4.21 (s, 1H), 4.01 (s, 1H), 3.88 (s, 1H), 2.87 (s, 4H), 2.80 (s, 3H), 2.36 (s, 3H), 1.90 (s, 2H), 1.67 (s, 4H).

Example 17: Preparation of Compound 1

To a solution of compound 8 (5.0 g, 26.4 mmol) in anhydrous MeOH (75 ml) was added compound 9 (6.42 g, 39.6 mmol), the mixture was heated to 50° C., keep stirring for 5 hours, the mixture was cooling to 0° C., NaBH4 (3.0 g, 79.2 mmol) was added by portions, the reaction mixture was continue stirring at room temperature for 4 hrs. The solvent was removed under reduced pressure and the residue was dissolved in ethyl acetate (75 ml), washed with saturated NaHCO₃ aqueous, water and brine, dried over Na₂SO₄, filtered and concentrated to give compound 1 (7.8 g, yield 88%).

Example 18: Preparation of Compound 1

To a solution of compound 8 (5.0 g, 26.4 mmol) in anhydrous MeOH (75 ml) was added compound 9 (5.35 g, 33 mmol), the mixture was heated to 70° C., keep stirring for 3 hours, the mixture was cooling to 0° C., NaBH4 (3.0 g, 79.2 mmol) was added by portions, the reaction mixture was continue stirring at room temperature for 4 hrs. The solvent was removed under reduced pressure and the residue was dissolved in ethyl acetate (75 ml), washed with saturated NaHCO₃ aqueous, water and brine, dried over Na₂SO₄, filtered and concentrated to give compound 1 (7.8 g, yield 88%).

Example 19: Preparation of Compound 1

To a solution of compound 8 (5.0 g, 26.4 mmol) in anhydrous MeOH (75 ml) was added compound 9 (4.28 g, 26.4 mmol), the mixture was heated to 60° C., keep stirring for 4 hours, the mixture was cooling to 0° C., NaBH4 (2.0 g, 52.8 mmol) was added by portions, the reaction mixture was continue stirring at room temperature for 4 hrs. The solvent was removed under reduced pressure and the residue was dissolved in ethyl acetate (75 ml), washed with saturated NaHCO₃ aqueous, water and brine, dried over Na₂SO₄, filtered and concentrated to give compound 1 (7.8 g, yield 88%).

Example 20: Preparation of Compound 1

To a solution of compound 8 (5.0 g, 26.4 mmol) in anhydrous MeOH (75 ml) was added compound 9 (4.28 g, 26.4 mmol), the mixture was heated to 60° C., keep stirring for 4 hours, the mixture was cooling to 0° C., NaBH4 (4.0 g, 105.6 mmol) was added by portions, the reaction mixture was continue stirring at room temperature for 4 hrs. The solvent was removed under reduced pressure and the residue was dissolved in ethyl acetate (75 ml), washed with saturated NaHCO₃ aqueous, water and brine, dried over Na₂SO₄, filtered and concentrated to give compound 1 (7.8 g, yield 88%).

In the specification, unless specified or limited otherwise, terms such as "first" and "second" are used herein for purposes of description and are not intended to indicate or imply relative importance or significance.

Reference throughout this specification to "an embodiment," "some embodiments," "one embodiment", "another example," "an example," "a specific examples," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example, "in an example," "in a specific examples," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A method for preparing a compound of formula 1, comprising steps of:
   (1) contacting a compound of formula 2 with acetic anhydride to obtain a compound of formula 3;
   (2) contacting the compound of formula 3 with a compound of formula 4 to obtain a compound of formula 5;
   (3) contacting the compound of formula 5 with polyphosphoric acid to obtain a compound of formula 6;
   (4) contacting the compound of formula 6 with borane-tetrahydrofuran to obtain a compound of formula 7;
   (5) contacting the compound of formula 7 with sodium hydroxide to obtain a compound of formula 8; and
   (6) contacting the compound of formula 8 with a compound of formula 9 to obtain the compound of formula 1,

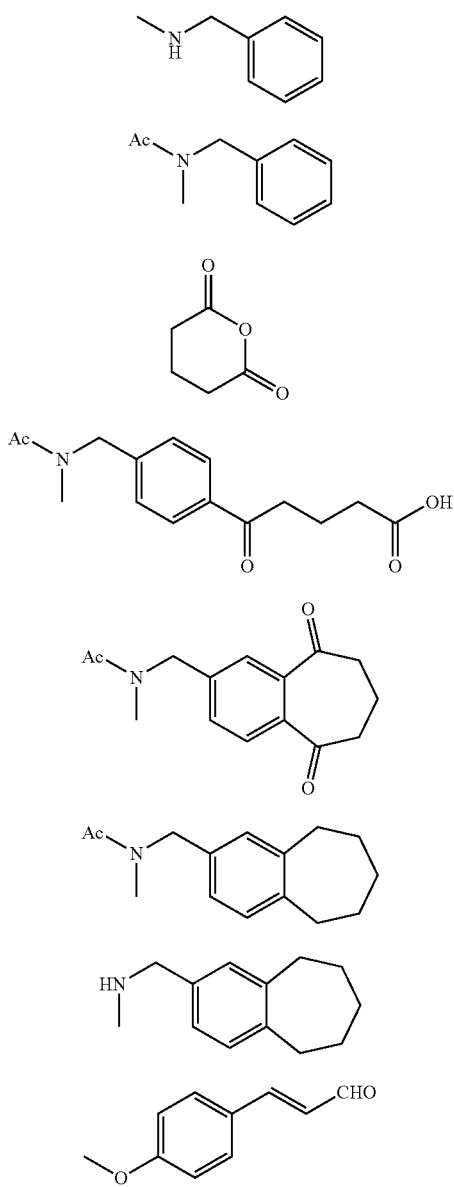

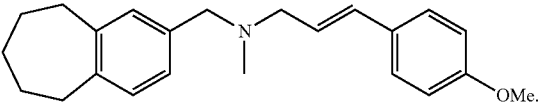

2. The method according to claim 1, wherein in the step (1), to a solution of the compound of formula 2 in dichloromethane (DCM) is added triethylamine, the mixture is cooled to 0° C., acetic anhydride is added dropwise with stirring; after the addition is completed, the reaction is continually stirred for 2 hours to 4 hours, monitored the reaction with TLC and when the result shows the reaction is completed, the solvent is removed under reduce pressure, and residence is washed with saturated NaHCO$_3$ aqueous, 10% citric acid aqueous and brine, dried over MgSO$_4$, filtered and concentrated to give the compound of formula 3.

3. The method according to claim 2, wherein the amount of triethylamine is 1.2 equivalents per 1 equivalent by mole of the compound of formula 2.

4. The method according to claim 2, wherein the amount of acetic anhydride is 1.05 equivalents to 1.3 equivalents per 1 equivalent by mole of the compound of formula 2.

5. The method according to claim 1, wherein in the step (2), the compound of formula 3 and the compound of formula 4 are dissolved in 1,2-dichlorobenzene, and the solution is added dropwise into a suspension of AlCl$_3$ in 1,2-dichlorobenzene with stirring, about 20 minutes later, the addition is completed, when there is no more HCl gas released, the reaction mixture is continually stirred for 1 hour, and poured into ice water, the aqueous layer is separated, and ethanol is added, the mixture is stirred and extracted thoroughly, and washed with ethanol repeated, and the mixture is dried under vacuum drying to give the compound of formula 5.

6. The method according to claim 5, wherein the amount of the compound of formula 4 is 1.01 equivalents to 1.2 equivalents per 1 equivalent by mole of the compound of formula 3.

7. The method according to claim 5, wherein the amount of AlCl$_3$ is 2 equivalents per 1 equivalent by mole of the compound of formula 3.

8. The method according to claim 1, wherein in the step (3), compound 5 is dissolved in polyphosphoric acid, the mixture is heated to a temperature ranging from about 80° C. to about 95° C., and stirring is kept for 3 hours to 6 hours, the reaction is completed, the mixture temperature is cooled to 45° C., water is poured with stirring, there exists white solid precipitate, and after filtering a filter cake is washed with water three times, after vacuum drying to give compound 6.

9. The method according to claim 8, wherein the amount of polyphosphoric acid is 10 equivalents to 20 equivalents per 1 equivalent by mole of the compound of formula 5.

10. The method according to claim 1, wherein in the step (4), the compound of formula 6 is dissolved in anhydrous THF, the mixture is cooled to 0° C. and protected by anhydrous nitrogen, borane-tetrahydrofuran complex is added dropwise; after the addition is completed, the reaction temperature is raised to room temperature slowly, and stirring is kept for 8 hours to 12 hours, the reaction is quenched by methanol, the solvent is removed under reduced pressure, the residue is dissolved in ethyl acetate, washed with saturated NaHCO$_3$ aqueous, water and brine, dried over anhydrous Na$_2$SO$_4$, filtered and concentrated to dryness to give the compound of formula 7.

11. The method according to claim 10, wherein the amount of borane-tetrahydrofuran is 3 equivalents to 5 equivalents per 1 equivalent by mole of the compound of formula 6.

12. The method according to claim 1, wherein in the step (5), the compound of formula 7 is dissolved in MeOH/1 N NaOH aq., the mixture is heated to a temperature ranging from about 50° C. to about 70° C. and stirring for 2 hours to 5 hours, the solvent is removed under reduced pressure, and extracted with DCM three times, combined the organic layer, dried over MgSO$_4$, filtered and concentrated to dryness to give the compound of formula 8.

13. The method according to claim 12, wherein the amount of MeOH is 1 equivalent per 1 equivalent by mole of the compound of formula 7.

14. The method according to claim 1, wherein in the step (6), to a solution of the compound of formula 8 in anhydrous MeOH is added the compound of formula 9, the mixture is heated to a temperature ranging from about 50° C. to about 70° C., stirring is kept for 3 hours to 5 hours, the mixture is cooled to 0° C., NaBH$_4$ is added by portions, the reaction mixture is continually stirring at room temperature for 4 hours; the solvent is removed under reduced pressure and the residue is dissolved in ethyl acetate, washed with saturated NaHCO$_3$ aqueous, water and brine, dried over Na$_2$SO$_4$, filtered and concentrated to give the compound of formula 1.

15. The method according to claim 14, wherein the amount of the compound of formula 9 is 1 equivalent to 1.5 equivalents per 1 equivalent by mole of the compound of formula 8.

16. The method according to claim 14, wherein the amount of NaBH$_4$ is 2 equivalents to 4 equivalents per 1 equivalent by mole of the compound of formula 8.

* * * * *